United States Patent [19]

Boitiaux et al.

[11] Patent Number: 4,849,577

[45] Date of Patent: Jul. 18, 1989

[54] PROCESS FOR ELIMINATING JOINTLY ARSENIC AND CARBON OXYSULFIDE FROM AN UNSATURATED HYDROCARBON CUT IN THE LIQUID PHASE

[75] Inventors: Jean-Paul Boitiaux, Poissy; Jean Cosyns, Maule, both of France

[73] Assignee: Institut Francais Du Petrole, Rueil-Malmaison, France

[21] Appl. No.: 168,809

[22] Filed: Mar. 16, 1988

[30] Foreign Application Priority Data

Aug. 7, 1987 [FR] France ................................ 8711347

[51] Int. Cl.$^4$ .......................... C07C 7/12; C10G 25/00
[52] U.S. Cl. ..................................... 585/820; 585/864; 585/855; 208/310 Z; 208/251 R; 208/230; 208/237; 208/249

[58] Field of Search ....................... 585/820, 864, 855; 208/310 Z, 251 R, 230, 237, 249

[56] References Cited

U.S. PATENT DOCUMENTS

| | | | |
|---|---|---|---|
| 1,581,369 | 4/1926 | Weir | 208/249 |
| 3,782,076 | 1/1974 | Carr et al. | 208/88 |
| 4,009,009 | 2/1977 | Massoth et al. | 55/73 |

Primary Examiner—Patrick P. Garvin
Assistant Examiner—E. D. Irzinski
Attorney, Agent, or Firm—Millen & White

[57] ABSTRACT

Process for eliminating jointly arsenic and carbon oxysulfide from an unsaturated hydrocarbon cut, wherein said hydrocarbon cut is contacted with an absorbing mass containing a support and lead oxide, comprising contacting the hydrocarbon cut in the liquid phase.

8 Claims, No Drawings

PROCESS FOR ELIMINATING JOINTLY ARSENIC AND CARBON OXYSULFIDE FROM AN UNSATURATED HYDROCARBON CUT IN THE LIQUID PHASE

BACKGROUND OF THE INVENTION

The various processes for cracking heavy petroleum cuts, such as catalytic cracking, visbreaking and coking, produce light cuts which are strongly contaminated by different compounds containing sulfur, nitrogen and oxygen. Arsenic is very often detected beside these impurities. The sulfur compounds most often are $H_2S$ and mercaptans. In the case of catalytic cracking, the presence of CO, $CO_2$ and COS is also noticed. The nitrogen compounds, which are present in the light cuts, are essentially ammonia or light amines. There is also arsenic itself in compound form with the general formula $As R_3$, R being for example a hydrocarbon radical such as $CH_3$ or a hydrogen atom.

SUMMARY OF THE INVENTION

What is here called light cuts are those which are gaseous under standard pressure and temperature conditions, that is to say $C_2$, $C_3$ and $C_4$ cuts. The latter cuts are generally treated in order to eliminate their sulfur compounds. Particularly $C_3$ and $C_4$ cuts are usually subjected to an amine washing treatment followed by a sodium hydroxide washing treatment. The various washing treatments almost totally eliminate $H_2S$, but only partly eliminate the organic sulfur compounds such as mercaptans and very incompletely eliminate COS.

Neither can the arsenic compounds be eliminated by these washings and thus they remain in the treated cuts.

Generally speaking, the $C_3$ and $C_4$ cuts, which contain an important amount of olefins, are a valuable raw material for the manufacturing of fuels or chemicals such as certain polymers. These modifications require various catalytic treatments in the course of which the catalysts are more or less quickly poisoned by the sulfur or the arsenic compounds. Thus, for example, the $C_3$ cut from the fluidized bed catalytic cracking (FCC) still has, after the washing treatments described above, COS contents from 1 to 50 ppm by weight and arsenic contents from 0.1 to 5 ppm by weight.

It is difficult to determine exactly the type of arsenic compound which is to be found in this cut. Still, it is generally observed that arsenic, after separation by distillation of the various light cuts, is principally found in $C_2$ and $C_3$ cuts.

They are therefore thought to be light arsines of the type $AsH_3$ or $AsH_2CH_3$.

The composition of the $C_3$ cuts from the catalytic cracking (FCC) is generally the following:

| | |
|---|---|
| Propane | 15-40% by weight |
| Propylene | 60-85% by weight |
| Propyne | 10-100 ppm |
| Propadiene | 10-100 ppm |
| $C_4$+ | 0.1-2% by weight |
| COS | 1-50 ppm |
| As | 0.1-5 ppm |

The important amount of propylene in this cut prompts the refiners to valorize it best, either as a raw material for the manufacturing of fuel by dimerization or alkylation with isobutane, or as a basic product for petrochemistry. In the latter case, the cut from the catalytic cracking is often valorized mixed with steam-cracking effluents. In the latter cuts, the propyne and propadiene amount is much higher and generally reaches in total 4 to 7% (sum propyne+propadiene). These compounds must be eliminated by selective hydrogenation, which is usually performed on a palladium-based catalyst. This catalyst is then very rapidly poisoned by arsenic and COS.

It has been well-known for a long time that lead oxide can absorb arsenic. A process for collecting arsenic in gaseous hydrocarbons using an absorbing mass composed of lead oxide deposited on a large surface alumina has been described more recently (U.S. Pat. No. 3,782,076). This patent recommends to operate at a relatively low pressure (less than about 20 bars), which means in the gaseous phase, in order to avoid polymerization parasitic reactions which would be favored by a pressure increase. The same patent also recommends to avoid the presence of $H_2S$, which seems to lessen the absorption efficiency of the collecting mass.

The use of lead oxide for absorbing carbon oxysulfide has also been described, but in this case the presence of arsenic must be excluded. It is also operated here at low pressure and, thus, in the gaseous phase.

On the contrary, it has now been discovered that it is possible to absorb jointly arsenic and carbon oxysulfide on condition that it is operated with hydrocarbons in the liquid phase, which means with relatively high pressures (over 20 bars). Besides, the catalyst deactivation with hydrocarbons in the liquid phase is less rapid than with reagents in the gaseous phase, especially when the stock contains acetylenic and/or diolefinic hydrocarbons. The results are still better when using an absorbing mass containing lead oxide and a "non acid" support, that is to say that the latter support should not catalyse the reactions known by the professionals as being catalysed by acid solids, namely isomerization reactions of the hydrocarbon skeleton, cracking and polymerization reactions. This support can for example be alumina, silica or magnesia. Alumina is preferably used because it enables obtaining both rather large specific surfaces and a sufficient mechanical resistance.

The acidity of the support can be determined by the well-known test of ammonia adsorption of the type described, for example, in "Journal of Catalysis, 2, 211-222 (1963)"; the method consists in heating the solid up to 600° C. under vacuum (which represents a pressure smaller than about 1 Pascal) until complete degassing (essentially in order to eliminate water and undesirable impurities); the support is then put into a calorimeter at 320° C. and a certain amount of ammonia is introduced so that the final pressure of the balanced system is about 40 kPa; the discharged heat amount is then measured. The ammonia adsorption heat measured under such conditions must be smaller than 40 joules per gram of support.

The support recommended by this invention is preferably an alumina with a surface from 10 to 300 m²/g, preferably from 50 to 200 m²/g. Its total pore volume is advantageously 0.2-1.2 cm³/g, preferably 0.5-1.2 cm³/g. The macropore volume, defined as the volume corresponding to the pores greater than 100 nm, is preferably 0.1-0.5 cm³/g.

The alumina supports which are commonly used for various hydrotreatings such as hydrodesulfurization and hydrodenitrogenation or those employed for the production of gasoline through the process of reforming are not suitable for the present invention. They actually show ammonia adsorption heats much greater than 40 joules per gram.

The supports used in this invention have various origins. One way of manufacturing them is pressure-heating a transition alumina with a specific surface from 200 to 400 m²/g under water steam pressure, then calcinating it at high temperature according to a method described in Patents FR Nos. 1,386,364, 1,449,904 and 1,584,460, in order to obtain an alumina with a surface smaller than 200 m²/g and the acidity of which, measured by ammonia adsorption, is smaller than 40 joules per gram. Another preferred way is that which consists in impregnating a transition alumina support (with a specific surface from 200 to 400 m²/g) with a salt of a metal from group VIII, such as cobalt or nickel, and then calcinate the impregnated solid at temperatures from 700° to 850° C., according to a technique described in Patent FR No. 2,118,309, in order to obtain as well a product with a surface smaller than 200 m²/g and an acidity smaller than 40 joules per gram.

The absorbing mass containing lead oxide is prepared by mixing a lead compound with the support, following well-known techniques. The method leading to the most performing mass is "dry" impregnation: filling up of the support pores with a volume equal to the pore volume of the support, the liquid being here an aqueous solution of a lead salt. Lead nitrate is an easily soluble lead salt; lead acetate is preferably used because it shows a good solubility and enables obtaining a collecting mass of a higher efficiency.

After impregnation of the support by the lead compound solution, it is brought to a temperature from 300° to 700° C., preferably 400°-550° C., in order to convert the lead compound into a lead oxide. This is preferably done in an oxygen-containing atmosphere.

The obtained masses advantageously contain from 5 to 50% lead by weight calculated as PbO.

The absorption is preferably achieved at a temperature from 10° to 100° C. under a pressure sufficient to maintain the cut to be treated in the liquid phase. The hourly volume flow rate of liquid stock per catalyst volume is advantageously 0.5–10, preferably 1–5.

The hydrocarbon stocks which are treated in the present invention can contain for example 0.1–20% of highly unsaturated hydrocarbons (acetylenic and diolefinic) by weight, most often 1–10%, and 0.1–20 ppm of arsenic, most often 0.5–5 ppm.

The following examples, which are not limiting, illustrate the present invention.

EXAMPLES

Example 1

In this example, various collecting masses have been prepared by dry impregnation, from an aqueous solution of trihydrated lead acetate and different alumina supports the main characteristics of which appear in Table 1.

TABLE 1

| Type of Support | specific surface m²/g | total pore volume cm³/g | macropore volume cm³/g (1) | acidity Δ H J/g (2) |
|---|---|---|---|---|
| Cubic gamma alumina | 205 | 0.60 | <0.01 | 60 |
| Pressure-heated | 70 | 0.63 | 0.17 | 13.6 |

TABLE 1-continued

| Type of Support | specific surface m²/g | total pore volume cm³/g | macropore volume cm³/g (1) | acidity Δ H J/g (2) |
|---|---|---|---|---|
| alumina | | | | |
| Pressure-heated alumina | 155 | 1.05 | 0.36 | 28 |
| Pretreated alumina (3) | 160 | 0.55 | 0.16 | 26 |

(1) The macropore volume corresponds to the cumulated volume of all the pores with a diameter equal to or greater than 100 nm.

(2) The acidity of the support has been measured according to the method described above.

(3) The pretreated alumina has been prepared by "dry" impregnation of a transition alumina with a surface of 250 m²/g and a total pore volume equal to 0.62 cm³/g with an aqueous solution of nickel nitrate. The nickel amount which was introduced represented 3% by weight in relation to the support. The solid has then been dried and calcinated under airstream at atmospheric pressure at a temperature of 750° C. for 2 hours.

The amount of lead acetate has been calculated to obtain collecting masses with 16% lead oxide by weight calculated as PbO. The impregnated solid has then been dried and treated under airstream at 450° C. for 2 hours. The four solids mentioned below have thus been obtained:

| No. | Designation |
|---|---|
| 1 | 16% PbO/cubic gamma Al₂O₃ |
| 2 | 16% PbO/70 m²/g pressure-heated Al₂O₃ |
| 3 | 16% PbO/155 m²/g pressure-heated Al₂O₃ |
| 4 | 16% PbO/pretreated Al₂O₃ |

A series of tests have then been achieved with a $C_3$ cut resulting partly from a steamcracking plant and partly from a fluid catalytic cracking plant (FCC). The composition of this cut was the following:

| | % by weight |
|---|---|
| Propane | 12.0 |
| Propylene | 83.2 |
| Propyne | 2.5 |
| Propadiene | 2.1 |
| $C_4$ | 0.2 |
| $C_5+$ | undetectable |
| COS | 5 ppm |
| As | 2.9 ppm |

50 cm³ of the absorbing mass to be tested was placed into a steel tube with a diameter of 3 cm. The solid was divided into 5 beds of 10 cm³ each, separated by glass wool buffers. The stock to be cleaned was given an upward flow in the following conditions:

Total pressure: 30 bars
Temperature: 50° C.
Liquid stock flow rate: 100 cm³/h (VVH=2)

The $C_3$ cut was made to pass for 10 hours. After this time, the composition of the product which was taken out of the reactor has been determined. The results for each mass appear in Table 2.

TABLE 2

| Hydrocarbons | Mass No. 1 | Mass No. 2 | Mass No. 3 | Mass No. 4 |
|---|---|---|---|---|
| Propane % by wt. | 12 | 12 | 12 | 12 |
| Propylene % by wt. | 83 | 83.2 | 83.2 | 83.2 |
| Propyne % by wt. | 1.6 | 2.5 | 2.5 | 2.5 |
| Propadiene % by wt. | 1.8 | 2.1 | 2.1 | 2.1 |
| $C_4$ % by wt. | 0.3 | 0.2 | 0.2 | 0.2 |
| $C_5+$ % by wt. | 1.3 | <0.1 | <0.1 | <0.1 |
| COS ppm | <0.1 | <0.1 | <0.1 | <0.1 |
| As ppb | <10 | <10 | <10 | <10 |

It can be seen from this table that mass No. 1, which was prepared on a support with an acidity greater than 40 J/g, produces a substantial amount of polymers ($C_5+$). This is a strong disadvantage because not only does it affect the efficiency of the operation, but it also causes a progressive obstruction of the absorbing mass pores, which decreases its absorbing effect.

In order to compare the adsorption efficiency of the various solids, the tests have been extended for over 500 hours.

After 500 hours, the arsenic and COS amounts in the product which came out of the reactor were measured. The obtained concentrations are shown in Table 3.

TABLE 3

| Mass | As (ppm) | COS (ppm) |
|---|---|---|
| 1 | 0.3 | 0.5 |
| 2 | <0.01 | <0.1 |
| 3 | <0.01 | <0.1 |
| 4 | <0.01 | <0.1 |

It can be seen that mass No. 1 is no longer totally effective after this time since it lets pass a substantial amount of arsenic and COS, contrarily to what has been observed with the masses used in this invention.

It can besides be noticed that mass No. 1, after 500 hours, still produces $C_5+$ hydrocarbons (about 1.3%), which affects the yield of the $C_3$ cut, contrarily to what has been observed for masses 2, 3 and 4 of the invention.

After 517 hours, the test was stopped and, after drying of the mass by nitrogen sweeping, the solid was unloaded bed by bed. The proportions by weight of arsenic and sulfur were measured for each bed. The results obtained for each mass are shown in Table 4.

TABLE 4

| | Mass No. 1 % by weight | | Mass No. 2 % by weight | | Mass No. 3 % by weight | | Mass No. 4 % by weight | |
|---|---|---|---|---|---|---|---|---|
| Beds | As | S | As | S | As | S | As | S |
| 1 | 0.30 | 0.27 | 0.66 | 0.70 | 0.71 | 0.75 | 0.68 | 0.73 |
| 2 | 0.23 | 0.21 | 0.30 | 0.22 | 0.27 | 0.17 | 0.29 | 0.19 |
| 3 | 0.18 | 0.16 | 0.04 | <0.05 | 0.02 | <0.05 | 0.03 | <0.05 |
| 4 | 0.11 | 0.10 | <0.02 | <0.05 | <0.02 | <0.05 | <0.02 | <0.05 |
| 5 | 0.08 | 0.07 | <0.02 | <0.05 | <0.02 | <0.05 | <0.02 | <0.05 |

It is to be noticed that, concerning the masses prepared following the invention, almost all of the arsenic and the sulfur have been fixed on the first two beds. The three fifths of these masses are still available for fixing these impurities after 517 hours. Very long periods of effective functioning may then be expected. On the contrary, concerning mass No. 1, prepared with an inadequate support, the whole solid is contaminated by arsenic and sulfur, which indicates that, at the end of the test, the adsorption of these impurities is no longer total, as shown in Table 1.

Example 2

In this example, a new collecting mass has been prepared, with the same support as mass No. 3, also containing 16% PbO, but the lead salt was no longer acetate but nitrate. The reactor was charged as in Example 1 and the same stock was treated in the same conditions as those described above. The test also lasted 517 hours; after this time, the solid was unloaded and analysed bed after bed. The arsenic and sulfur concentrations found on each bed are reported in Table 5.

TABLE 5

| Absorbing mass | Arsenic % by weight | Sulfur % by weight |
|---|---|---|
| 1st bed | 0.52 | 0.54 |
| 2nd bed | 0.25 | 0.21 |
| 3rd bed | 0.13 | 0.11 |
| 4th bed | 0.08 | 0.06 |
| 5th bed | 0.02 | <0.05 |

If these results are compared to those in Table 4 (mass No. 3), it will be noticed that, after the same time, the four fifths of the mass are contaminated, instead of about two fifths of the mass prepared with lead acetate.

These results are however better than those of mass No. 1 in Example 1.

Moreover, as in Example 1, the mass prepared according to the invention leaves the composition of the hydrocarbon cut unchanged; there is so no detectable formation of heavy hydrocarbons ($C_5+ <0.1\%$).

Example 3 (comparison example)

Example 1 was repeated identically with the mass No. 3, except that the pressure was 15 bars, at which pressure the feed stock was entirely in the gaseous phase.

After 500 hours of this gaseous phase operation, the product discharged from the reactor was analyzed and found to contain:

As: 0.1 ppm by weight
COS: 0.2 ppm by weight which values may be compared with those in Table 3 (mass No. 3).

After 517 hours, the mass No. 3 was discharged as disclosed in Example 1 and found to comprise:

| Bed | % As by weight | % S by weight |
|---|---|---|
| 1st | 0.36 | 0.33 |
| 2nd | 0.28 | 0.26 |
| 3rd | 0.15 | 0.13 |
| 4th | 0.07 | 0.06 |
| 5th | 0.04 | 0.03 |

By comparison with Table 4 (mass No. 3), it can be seen that the absorbing mass has a lower yield when operating in the gaseous phase instead of the liquid phase: all the beds are contaminated with arsenic and sulfur instead of only the first two beds in the liquid phase.

We claim:

1. A process for simultaneously eliminating arsenic and carbon oxysulfide from an unsaturated hydrocarbon cut, comprising contacting said hydrocarbon cut in the liquid phase with an absorbing mass containing a support and lead oxide.

2. A process according to claim 1, wherein said mass results from (a) admixing of a solution of a soluble lead compound with an alumina support with a surface from 10 to 300 m$^2$/g, a pore volume from 0.2 to 1.2 cm$^3$/g, a macropore volume, calculated for the pores greater than 100 nm, from 0.1 to 0.5 cm$^3$/g and an acidity, measured by the ammonia adsorption heat under 40 kPa at 320° C., smaller than 40 joules per gram of support, and (b) heating from 500° to 900° C. in an oxygen-containing atmosphere.

3. A process according to claim 2, wherein the alumina support has a surface from 50 to 200 m$^2$/g and a total pore volume from 0.5 to 1.2 cm$^3$/g.

4. A process according to claim 2, wherein the soluble lead compound is lead acetate.

5. A process according to claim 1, wherein the mass comprises 5 to 50% lead by weight, calculated as PbO.

6. A process according to claim 1, wherein the hydrocarbon cut is at least one $C_2$, $C_3$ or $C_4$ olefinic cut.

7. A process according to claim 1, wherein the hydrocarbon cut comprises propylene.

8. A process according to claim 3, wherein the alumina support is alumina which has been heated under steam pressure.

* * * * *